United States Patent
Frenkel et al.

(10) Patent No.: US 7,368,581 B2
(45) Date of Patent: *May 6, 2008

(54) PROCESS FOR THE PREPARATION OF FLUVASTATIN SODIUM CRYSTAL FROM XIV

(75) Inventors: Gustavo Frenkel, Beer Sheva (IL); Eyal Gilboa, Bat-Yam (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 297 days.

This patent is subject to a terminal disclaimer.

(21) Appl. No.: 10/920,112

(22) Filed: Aug. 17, 2004

(65) Prior Publication Data

US 2005/0119342 A1    Jun. 2, 2005

Related U.S. Application Data

(63) Continuation-in-part of application No. 10/871,916, filed on Jun. 18, 2004.

(60) Provisional application No. 60/545,466, filed on Feb. 19, 2004, provisional application No. 60/507,954, filed on Oct. 3, 2003, provisional application No. 60/493,793, filed on Aug. 11, 2003, provisional application No. 60/485,748, filed on Jul. 10, 2003, provisional application No. 60/483,099, filed on Jun. 30, 2003, provisional application No. 60/479,182, filed on Jun. 18, 2003.

(51) Int. Cl.
*C07D 209/12* (2006.01)
(52) U.S. Cl. .................................... 548/494
(58) Field of Classification Search .............. 548/494
See application file for complete search history.

(56) References Cited

U.S. PATENT DOCUMENTS

| 4,739,073 A | 4/1988 | Kathawala |
| 5,189,164 A | 2/1993 | Kapa et al. |
| 5,354,772 A | 10/1994 | Kathawala |
| 6,124,340 A | 9/2000 | Horvath |
| 6,696,479 B2 | 2/2004 | Van Der Schaaf et al. |
| 2003/0032666 A1 | 2/2003 | Van Der Schaaf et al. |
| 2005/0032884 A1 | 2/2005 | Lifshitz-Liron et al. |
| 2005/0038114 A1* | 2/2005 | Lifshitz-Liron et al. .... 514/548 |

FOREIGN PATENT DOCUMENTS

| EP | 0 363 934 | 4/1990 |
| WO | WO 00/53566 | 9/2000 |
| WO | WO 02/36563 | 5/2002 |
| WO | WO 03/013512 A | 2/2003 |

OTHER PUBLICATIONS

Lundberg, ed., "The Lipid Research Clinics Coronary Primary Prevention Trial Results: 1. Reduction In Incidence Of Coronary Heart Disease", *J.A.M.A.*, 1984, pp. 351-374, vol. 251, No. 3.

Scandinavian Simvastatin Survival Study Group, "Randomised Trial Of Cholesterol Lowering In 4444 Patients With Coronary Heart Disease: The Scandinavian Survival Study (4s)", *The Lancet*, 1994, pp. 1383-1389, vol. 344.

Tang, et al., Synthesis Of Carbon-14 Labeled Fluvastatin (Lescol®), *Journal of Labeled Compounds & Radiopharmaceuticals*, 1998, pp. 1-7, vol. XLI, No. 1.

Witztum, "Chapter 36: Drugs Used In The Treatment Of Hyperlipoproteinemias", *Goodman and Gilman's The Pharmacological Basis of Therapeutics*, 9th ed., 1996, pp. 875-897.

* cited by examiner

*Primary Examiner*—Kamal A. Saeed
*Assistant Examiner*—Rei-tsang Shiao
(74) *Attorney, Agent, or Firm*—Kenyon & Kenyon LLP

(57) ABSTRACT

Provided is a process for preparing a polymorphic form of fluvastatin sodium, particularly Form XIV.

17 Claims, 6 Drawing Sheets

PROCESS FOR THE PREPARATION OF FLUVASTATIN SODIUM CRYSTAL FROM XIV

CROSS-REFERENCE TO RELATED APPLICATIONS

This application is a continuation-in-part of U.S. patent application Ser. No. 10/871,916, filed Jun. 18, 2004, which claims the benefit of U.S. Provisional Application Ser. Nos. 60/479, 182, filed Jun. 18, 2003; 60/483,099, filed Jun. 30, 2003; 60/485,748, filed Jul. 10, 2003; 60/493,793, filed Aug. 11, 2003; 60/507,954, filed Oct. 3, 2003 and 60/545,466, filed Feb. 19, 2004, all of which are incorporated herein by reference.

FIELD OF THE INVENTION

The present invention relates to the antihypercholesterolemia and antilipidemia agent fluvastatin and, more particularly, to the solid state properties of its monosodium salt.

BACKGROUND OF THE INVENTION

Complications of cardiovascular disease, such as myocardial infarction, stroke, and peripheral vascular disease account for half of the deaths in the United States. A high level of low density lipoprotein (LDL) in the bloodstream has been linked to the formation of coronary lesions which obstruct the flow of blood and can rupture and promote thrombosis. Goodman and Gilman, *The Pharmacological Basis of Therapeutics* 879 (9th ed. 1996). Reducing plasma LDL levels has been shown to reduce the risk of clinical events in patients with cardiovascular disease and in patients who are free of cardiovascular disease but who have hypercholesterolemia. Scandinavian Simvastatin Survival Study Group, 1994; Lipid Research Clinics Program, 1984a, 1984b.

Statin drugs are currently the most therapeutically effective drugs available for reducing the level of LDL in the blood stream of a patient at risk for cardiovascular disease. This class of drugs includes, inter alia, compactin, lovastatin, simvastatin, pravastatin and fluvastatin. The mechanism of action of statin drugs has been elucidated in some detail. They disrupt the synthesis of cholesterol and other sterols in the liver by competitively inhibiting the 3-hydroxy-3-methyl-glutaryl-coenzyme A reductase enzyme ("HMG-CoA reductase"). HMG-CoA reductase catalyzes the conversion of HMG-CoA to mevalonate, which is the rate determining step in the biosynthesis of cholesterol. Consequently, its inhibition leads to a reduction in the rate of formation of cholesterol in the liver.

[R*,S*-(E)]-(±)-7-[3-(4-fluorophenyl)-1-(1-methylethyl)-1H-indol-2-yl]-3,5-dihydroxy-6-heptenoic acid is a statin drug. It is known by the trivial name fluvastatin and has the molecular formula (I):

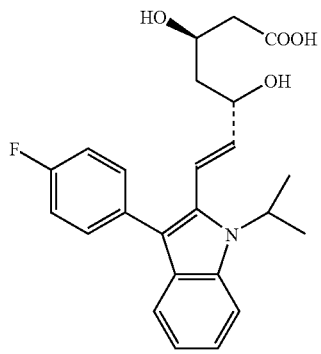

Fluvastatin depicted in free acid form.

Fluvastatin is commercially available under the trade name Lescol®. Fluvastatin is supplied as a monosodium salt in capsules containing the equivalent of 20 and 40 mg of fluvastatin and in extended-release tablets containing the equivalent of 80 mg of fluvastatin. Fluvastatin and its sodium salt are described in U.S. Pat. No. 4,739,073. In Example 6(a) of the '073 patent, a methyl ester precursor of (±) fluvastatin was hydrolyzed with sodium hydroxide in methanol, which yielded, after evaporation of the methanol, crude fluvastatin sodium. In Example 6(b), the fluvastatin methyl ester was hydrolyzed with sodium hydroxide in ethanol. After evaporation of the ethanol, the residue was taken up in water and lyophilized. The lyophilized product had a melting point range of 194□C-197□C. In Example 8, the sodium salt was prepared by ring opening of fluvastatin lactone with sodium hydroxide in ethanol as described in Example 6(b). The product of Example 8 produced an infrared spectrum in a KBr pellet with bands at: 3413, 2978, 2936, 1572 and 1216 cm$^{-1}$.

According to U.S. Pat. No. 6,124,340, lyophilization of fluvastatin sodium as was performed in Examples 6(b) and 8 of the '073 patent yields solid fluvastatin sodium as a mixture of a crystalline form, designated as Form A, and amorphous material. The '340 patent sets forth the spectroscopic properties of another crystal form of fluvastatin sodium which is said to have low hygroscopicity and photostability. This other form is called Form B in the '340 patent. It is characterized by an infrared spectrum with bands at 3343, 2995, 1587, 1536, 1386, 1337, 1042 and 1014 cm$^{-1}$ and by the following powder X-ray diffraction peak positions and intensities.

| °2θ | d (Å) | I/I$_O$(%) |
|---|---|---|
| 4.063 | 21.728 | 100 |
| 11.056 | 7.996 | 2.9 |
| 11.328 | 7.805 | 5.5 |
| 12.210 | 7.243 | 45.2 |
| 12.965 | 6.823 | 34.6 |
| 14.925 | 5.931 | 9.3 |
| 15.277 | 5.795 | 4.5 |
| 15.750 | 5.622 | 18.5 |
| 16.350 | 5.417 | 10.6 |
| 17.760 | 4.990 | 17.6 |
| 18.320 | 4.839 | 14.3 |
| 18.875 | 4.698 | 11.3 |
| 19.396 | 4.573 | 7.0 |
| 19.701 | 4.503 | 13.4 |
| 20.395 | 4.351 | 13.5 |
| 21.329 | 4.163 | 8.5 |
| 21.785 | 4.076 | 15.9 |
| 22.610 | 3.929 | 7.5 |
| 23.868 | 3.725 | 5.4 |
| 24.281 | 3.663 | 3.6 |
| 24.463 | 3.636 | 3.6 |
| 25.446 | 3.498 | 5.6 |
| 25.655 | 3.470 | 3.6 |
| 26.357 | 3.379 | 3.3 |
| 27.040 | 3.295 | 2.8 |
| 28.747 | 3.103 | 3.4 |
| 29.940 | 2.982 | 2.8 |
| 32.165 | 2.781 | 1.6 |
| 35.173 | 2.549 | 1.0 |
| 37.131 | 2.419 | 1.3 |

Fluvastatin sodium Form A is said to have the following powder X-ray diffraction peak positions and intensities.

| °2θ | d (Å) | I/I₀ (%) |
|---|---|---|
| 3.965 | 22.265 | 100 |
| 7.936 | 11.131 | 0.9 |
| 10.554 | 8.375 | 1.7 |
| 10.645 | 8.304 | 1.5 |
| 11.931 | 7.412 | 44.5 |
| 12.215 | 7.240 | 14.5 |
| 14.496 | 6.106 | 1.1 |
| 14.812 | 5.976 | 0.8 |
| 15.916 | 5.564 | 0.3 |
| 17.769 | 4.988 | 3.2 |
| 18.640 | 4.756 | 5.3 |
| 19.856 | 4.468 | 5.8 |
| 20.518 | 4.325 | 2.9 |
| 20.908 | 4.245 | 1.2 |
| 21.389 | 4.151 | 1.3 |
| 21.722 | 4.088 | 1.1 |
| 22.675 | 3.918 | 0.8 |
| 24.089 | 3.691 | 1.0 |
| 24.533 | 3.626 | 0.5 |
| 26.519 | 3.358 | 0.2 |
| 27.973 | 3.187 | 0.9 |
| 28.861 | 3.091 | |

U.S. Patent Application Publication No. 2003/0032666 reports the existence of four crystal forms of fluvastatin monosodium called Forms C, D, E and F. The water content of the forms ranges between 3 and 32%. The new crystal forms of fluvastatin sodium were obtained by storing the samples under atmospheres ranging between 20 and 90% relative humidity.

According to the '666 publication, the PXRD pattern of fluvastatin sodium Form C possesses characteristic peaks at the following d-values and qualitative intensities:

| d (Å) | Intensity |
|---|---|
| 23.8 | (vs) |
| 11.8 | (w) |
| 7.8 | (vs) |
| 7.6 | (vw) |
| 7.4 | (vw) |
| 6.4 | (vw) |
| 6.1 | (vw) |
| 5.90 | (w) |
| 5.00 | (vw) |
| 4.88 | (w) |
| 4.73 | (m) |
| 4.56 | (w) |
| 4.40 | (vw) |
| 4.12 | (vw) |
| 4.03 | (vw) |
| 3.96 | (vw) |
| 3.50 | (vw) |
| 3.36 | (vw) |
| 2.93 | (vw) | wherein
(vs) = very strong intensity;
(s) = strong intensity;
(m) = medium intensity;
(w) = weak intensity;
and (vw) = very weak intensity.

According to the '666 publication, the PXRD pattern of fluvastatin sodium Form D possesses characteristic peaks at the following d-values and qualitative intensities:

| d (Å) | Intensity |
|---|---|
| 24.6 | (vs) |
| 12.5 | (w) |
| 8.3 | (vs) |
| 7.4 | (vw) |
| 6.2 | (m) |
| 4.97 | (w) |
| 4.85 | (vw) |
| 4.52 | (vw) |
| 4.40 | (vw) |
| 4.14 | (vw) |
| 3.96 | (vw) |
| 3.41 | (vw) |
| 3.10 | (vw) |

According to the '666 publication, the PXRD pattern of fluvastatin sodium Form E possesses characteristic peaks at the following d-values and qualitative intensities:

| d (Å) | Intensity |
|---|---|
| 27.6 | (m) |
| 13.9 | (vw) |
| 9.2 | (m) |
| 8.5 | (vw) |
| 8.1 | (vw) |
| 7.4 | (vw) |
| 6.9 | (s) |
| 6.1 | (vw) |
| 4.98 | (m) |
| 4.77 | (m) |
| 4.63 | (m) |
| 4.15 | (w) |
| 4.03 | (w) |
| 3.97 | (vw) |
| 3.52 | (vw) |
| 3.33 | (vw) |
| 3.08 | (vw) |
| 2.99 | (vw) |

According to the '666 publication, the PXRD pattern of fluvastatin sodium Form F possesses characteristic peaks at the following d-values and qualitative intensities:

| d (Å) | Intensity |
|---|---|
| 29.6 | (w) |
| 14.8 | (vw) |
| 9.9 | (w) |
| 8.6 | (vw) |
| 8.3 | (vw) |
| 7.4 | (s) |
| 6.6 | (vw) |
| 6.2 | (vw) |
| 5.93 | (w) |
| 5.03 | (m) |
| 4.94 | (m) |
| 4.35 | (vw) |
| 4.23 | (w) |
| 3.98 | (vw) |
| 3.54 | (vw) |
| 2.98 | (vw) |

It also deserves mention that International Publication No. WO 02/36563 discloses crystal forms of enantiomerically pure [3R,5S] and [3S,5R] fluvastatin sodium.

The present invention also relates to fluvastatin sodium and the properties that it can exhibit in the condensed phase. The occurrence of different crystal forms (polymorphism) is a property of some molecules and molecular complexes. A single molecule, like the fluvastatin in formula (I) or a salt complex like fluvastatin sodium, may give rise to a variety of solids having distinct physical properties like melting point, X-ray diffraction pattern, infrared absorption fingerprint and NMR spectrum. The crystalline form may give rise to thermal behavior different from that of the amorphous material or another crystalline form. Thermal behavior is measured in the laboratory by such techniques as capillary melting point, thermogravimetric analysis ("TGA") and differential scanning calorimetry ("DSC") and can be used to distinguish some polymorphic forms from others. The differences in the physical properties of different crystalline forms result from the orientation and intermolecular interactions of adjacent molecules (complexes) in the bulk solid. Accordingly, polymorphs are distinct solids sharing the same molecular formula yet having distinct advantageous and/or disadvantageous physical properties compared to other forms in the polymorph family. These properties can be influenced by controlling the conditions under which the salt is obtained in solid form.

Exemplary solid state physical properties include the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

One of the most important physical properties of pharmaceutical polymorphs is their solubility in aqueous solution, particularly their solubility in the gastric juices of a patient. For example, where absorption through the gastrointestinal tract is slow, it is often desirable for a drug that is unstable to conditions in the patient's stomach or intestine to dissolve slowly so that it does not accumulate in a deleterious environment. On the other hand, the method is not advantageous where the effectiveness of a drug correlates with peak bloodstream levels of the drug, as in the case of statin drugs. With a statin drug, provided the drug is rapidly absorbed by the GI system, a more rapidly dissolving form is likely to exhibit increased effectiveness over a comparable amount of a more slowly dissolving form.

It is often the case that the most rapidly dissolving solid state of a compound is amorphous. Amorphous forms are often less stable than crystalline forms because they do not have many of the stabilizing intermolecular interactions that are present in crystalline forms. With an amorphous form, therefore, stabilizing intermolecular interactions do not have to be broken when the compound goes into solution, and so the dissolution rate is not retarded. Although they are more rapidly dissolving than crystalline forms, amorphous forms of a compound can have disadvantages. A compound, when it is in an amorphous state, is frequently more hygroscopic than a crystalline form of the same compound (although exceptions abound, such as when the crystal has wide channels that allow water to enter and leave the crystal in response to changes in moisture density outside the crystal). Water has been implicated in drug stability problems. For instance, the decomposition of aspirin which leads to the characteristic smell of vinegar when an old bottle of aspirin is opened is a hydrolysis reaction catalyzed by water. It is thus prudent when selecting a solid state form of a compound that is to be used as a drug, and possibly stored for a long time between packaging and use, to select a form that has low permeability to water. In the case of fluvastatin monosodium, a crystalline form designated Form B has already been discovered that is purportedly less hygroscopic than the partially crystalline/partially amorphous form of the salt that is obtained by following procedures in U.S. Pat. No. 4,739,073.

Although six distinct crystalline forms of racemic fluvastatin sodium have been reported to date, and at least one of them is purported to be less hygroscopic that the solid state form originally reported by the discovers of the compound, the discovery of yet other crystalline forms of fluvastatin sodium is desirable. The discovery of new crystalline forms and solvates of a pharmaceutically useful compound provides a new opportunity to improve the performance characteristics of a pharmaceutical product by enlarging the repertoire of materials that a formulation scientist has available for designing. For example, new crystalline forms can be used to design a pharmaceutical dosage form of a drug with low hygroscopicity, a targeted release profile, consistent dosing (enabled by good flow of the tableting composition into the tableting die), or other desired characteristic. New polymorphic forms and solvates of fluvastatin have now been discovered.

SUMMARY OF THE INVENTION

Figure 1:
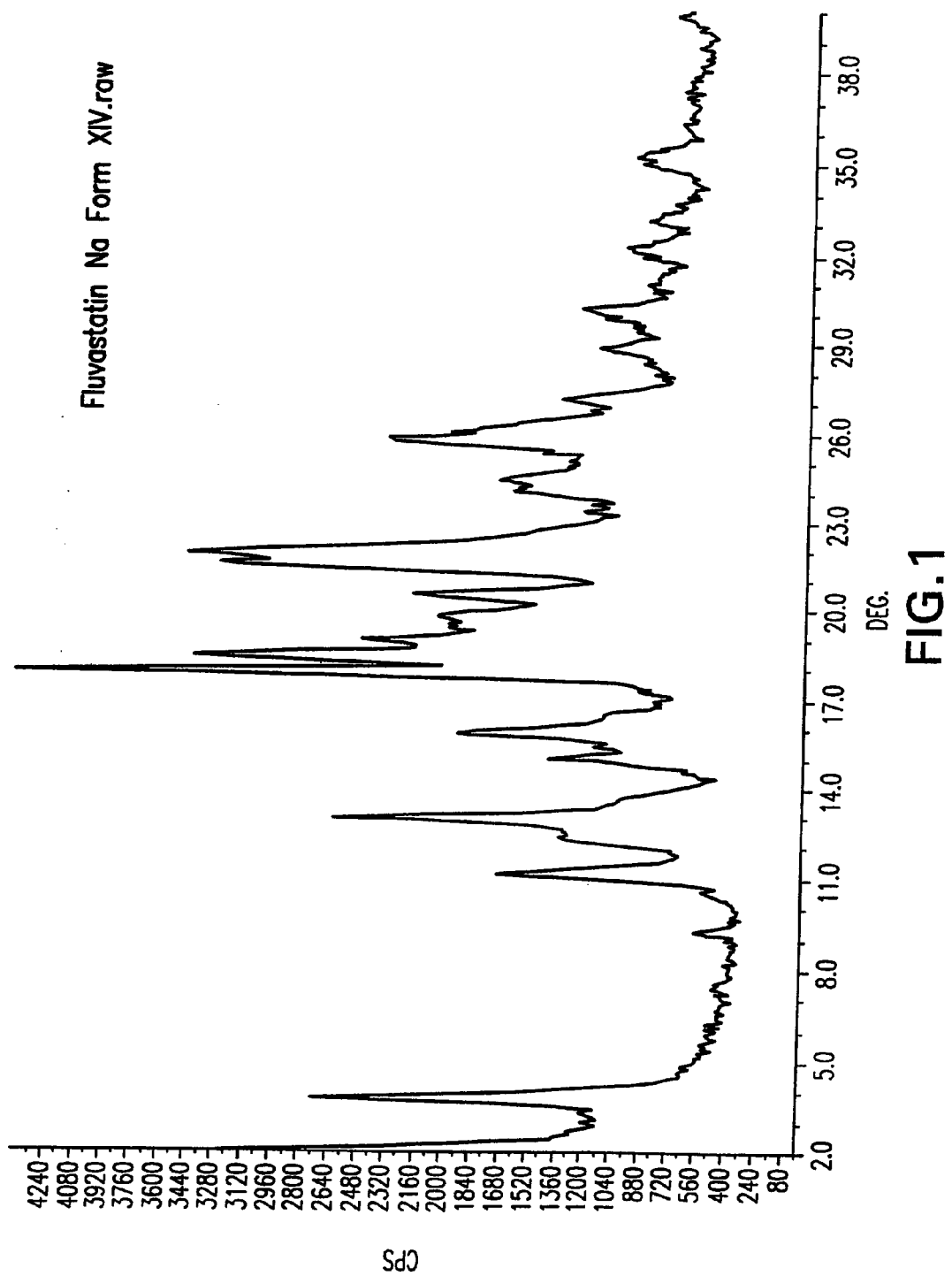
FIG. 1 depicts a powder X-ray diffractogram of fluvastatin sodium Form XIV.

In one aspect, the present invention provides a process for preparing a crystalline form of fluvastatin sodium characterized by a PXRD pattern with peaks at 3.8, 11.1, 12.9, 17.8 and 21.7±0.2 degrees two-theta comprising:
  a) combining a $C_1$ to $C_4$ alkyl ester of fluvastatin with acetonitrile at a ratio of about 1:4-6 (Kg/L) of the ester to acetonitrile, and with water at a ratio of about 1:1.3-1:2 (Kg/L) of the ester to the water, to obtain a mixture;
  b) combining sodium hydroxide with the mixture to hydrolyze the ester, thereby obtaining a solution, wherein if aqueous sodium hydroxide is used, the water ratio does not exceed that provided in step (a);
  c) combining additional acetonitrile with the solution to precipitate crystalline fluvastatin sodium; and
  d) recovering crystalline fluvastatin sodium.

Preferably, the alkyl ester is combined with acetonitrile at a ratio of about 1 :5-6(Kg/L). Preferably, the addition of the acetonitrile in step (c) results in a ratio of about 1:15 to about 1:25 (Kg/L), more preferably about 1:19.5-1:20.5 (Kg/L). Preferably, the ratio of the ester to water is about 1:1.3-1:1.8 (Kg/L). Preferably, the solution is maintained after addition of acetonitrile for about 2 to about 24 hours, more preferably for about 5 hours. Preferably, prior to combining with acetonitrile, the mixture is heated to a temperature of about 30° C. to about 40° C. to facilitate dissolution. More preferably, the mixture is heated to a temperature of about 35° C. Preferably, after heating, the solution is cooled to room temperature. Preferably, the ester is t-butyl. When a butyl ester is not used, preferably the ratio is calculated based on the weight of butyl ester.

In another aspect, the present invention provides a process for preparing a crystalline form of fluvastatin sodium characterized by a PXRD pattern with peaks at 3.8, 11.1, 12.9, 17.8 and 21.7±0.2 degrees two-theta comprising:
  a) preparing a solution of fluvastatin sodium in acetonitrile at a ratio of about 1:4-6 (Kg/L) of fluvastatin to acetonitrile, and in water at a ratio of about 1:1.3-1:2 (Kg/L) of fluvastatin to water, wherein the ratio is based on the molar weight of butyl ester of fluvastatin;
  b) combining the solution with an additional amount of acetonitrile to precipitate the crystalline fluvastatin sodium; and
  c) recovering the crystalline fluvastatin sodium.

Preferably the fluvastatin to acetonitrile ratio is about 1:5-6 (Kg/L). Preferably addition of acetonitrile in step (b) results in a ratio of about 1:15-1:25 (Kg/L), more preferably about 1:19.5 to 1:20.5 (Kg/L). Preferably the ratio of fluvastatin to water is about 1:1.3-1:1.8 (Kg/L).

In another aspect, the present invention provides a pharmaceutical composition comprising an effective amount of a fluvastatin sodium form having a PXRD pattern (Form XIV) 3.8, 11.1, 12.9, 17.8 and 21.7±0.2 degrees two-theta and a pharmaceutically acceptable excipient. Also provided are pharmaceutical dosage forms from such compositions such as tablets. Also provided are methods of treating a patient suffering from hypercholesterolemia or hyperlipidemia comprising the step of administering to the patient an effective amount of this pharmaceutical composition.

DETAILED DESCRIPTION OF THE PREFERRED EMBODIMENTS

As used in this disclosure, the term "elevated temperature" means a temperature above ambient temperature or above about 25° C. Preferred elevated temperatures are 50° C. and above and especially preferred elevated temperatures, when used in reference to contacting with particular liquids, are the boiling points of such liquids.

The term "lower alkyl" means a $C_1$ to $C_4$ alkyl group.

The terms "suspend" or "slurry" refer to a heterogeneous mixture where complete dissolution does not occur.

The present invention provides for a crystal form of [R*,S*-(E)]-(±)-7-[3-(4-fluorophenyl)-1-(1-methylethyl)-1H-indol-2-yl]-3,5-dihydroxy-6-heptenoic acid monosodium (fluvastatin sodium). The crystalline form of fluvastatin sodium has been designated Forms XIV. In so doing we have opted to use Roman numerals as labels for the crystals instead of the Roman alphabetical labels used by others working in the field to label other crystalline forms of fluvastatin sodium.

Whether the two enantiomers of [R*,S*-(E)]-(±) fluvastatin sodium co-crystallize in a single unit cell or whether they crystallize in separate unit cells that are mirror images of each other has yet to be determined for all of the new crystals forms. Accordingly, the crystal form of this invention is considered to include crystals that exhibit substantially the same PXRD patterns as those depicted in the figures whether they are prepared starting from pure or enriched [R*,S*-(E)]-(+) and [R*,S*-(E)]-(−) fluvastatin sodium or racemic fluvastatin sodium.

By the crystallization processes of this invention fluvastatin sodium Form XIV is obtained substantially free from other crystal forms, which means less than 5% of any other crystal form as measured by X-ray powder diffraction. The XRD pattern of Form B is significantly different from the XRD pattern of the novel crystal forms. Several XRD peaks of Form B are not overlapping with the XRD peaks of the novel forms. Detection of Form B is possible at 12.2, 16.4 and 22.6±0.2 degrees two theta.

Fluvastatin Form XIV is a hydrated form of fluvastatin sodium. The level of water in fluvastatin sodium is measured by Karl Fisher using methods known in the art. Some of the new crystal forms of fluvastatin sodium contain residual solvent in addition to water, which is seen by the fact that the TGA weight loss value is significantly larger than the Karl Fisher value. Some of the solvated crystal forms contain only small quantities of residual solvent. Fluvastatin sodium Form XIV can be found in the following hydrated states: monohydrate sesquihydrate, dihydrate (water content about 7-8%); trihydrate (water content about 11-13%); tetrahydrate (water content about 14-16%); hemipentahydrate, pentahydrate (water content 17-18%); Form XIV can be obtained with less than about 6% water, even as low as about 3% water by weight.

Fluvastatin is a known compound that can be purchased from commercial sources or synthesized by known processes such as the process disclosed in U.S. Pat. No. 4,739,073, which is incorporated herein by reference in its entirety. In particular, U.S. Pat. No. 4,739,073 is incorporated herein for its disclosure of how to prepare fluvastatin and fluvastatin sodium. In the processes of this invention that use fluvastatin sodium as a starting material, fluvastatin sodium Form B is the preferred starting material unless otherwise indicated.

Figure 2:
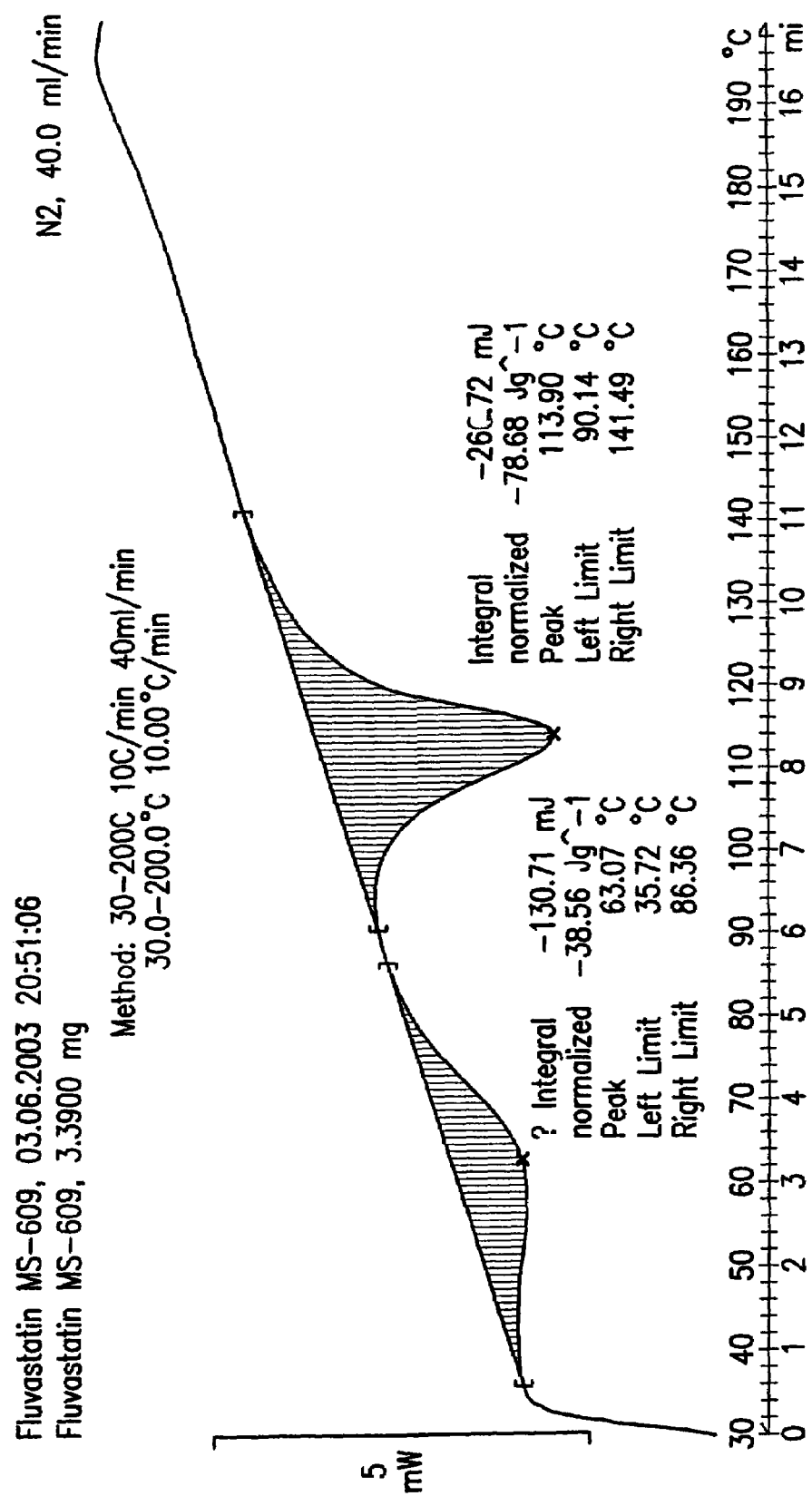
FIG. 2 depicts a DSC thermogram of fluvastatin sodium Form XIV.
Figure 3:
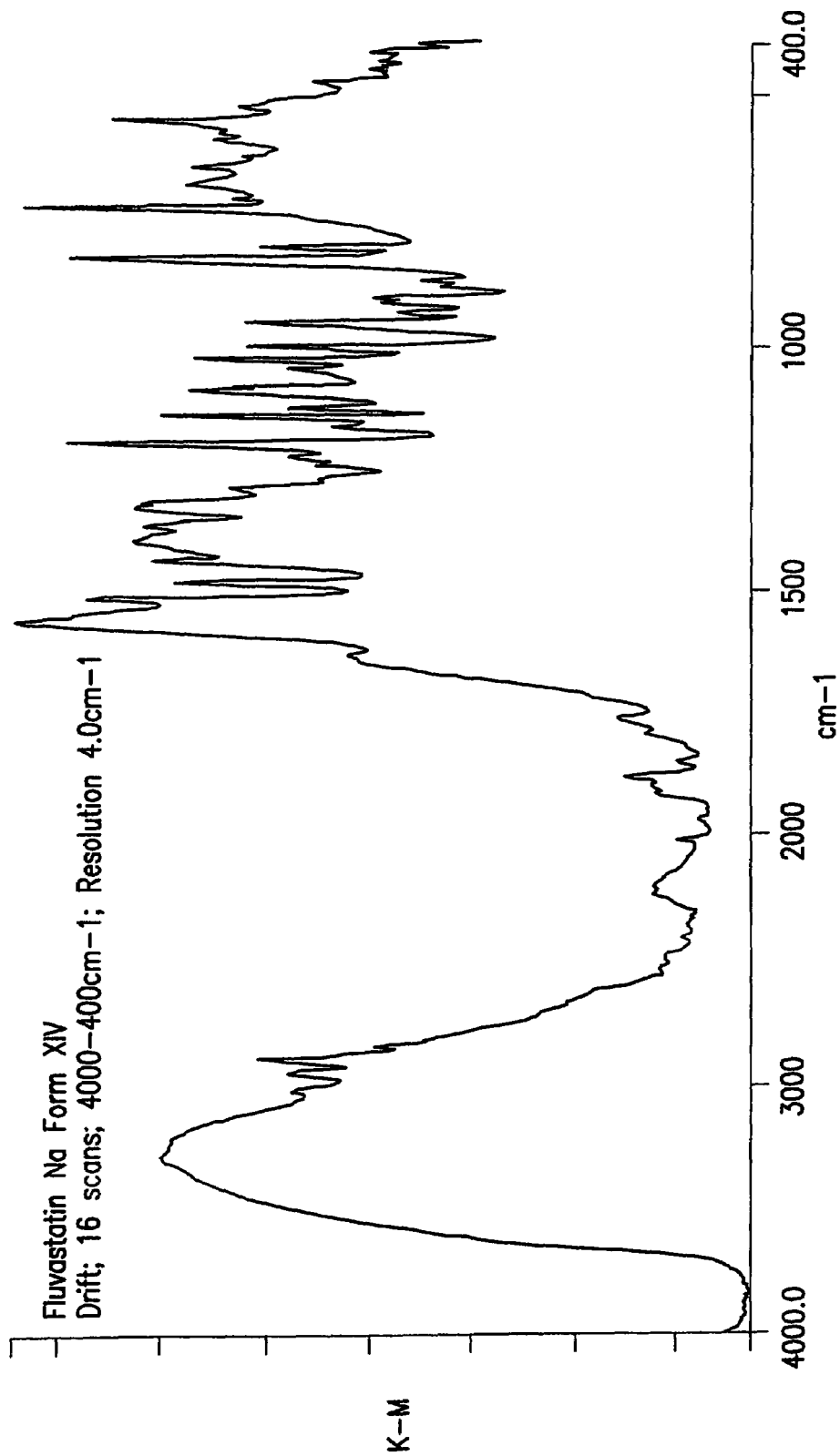
FIG. 3 depicts an IR spectrum of fluvastatin sodium Form XIV scanned from 4000 to 400 cm$^{-1}$, while FIG. 3a expands the 4000-1500 cm.$^{-1}$ region of the spectrum and FIG. 3b expands the 1500–400 cm$^{-1}$ region of the spectrum.
Figure 3A:
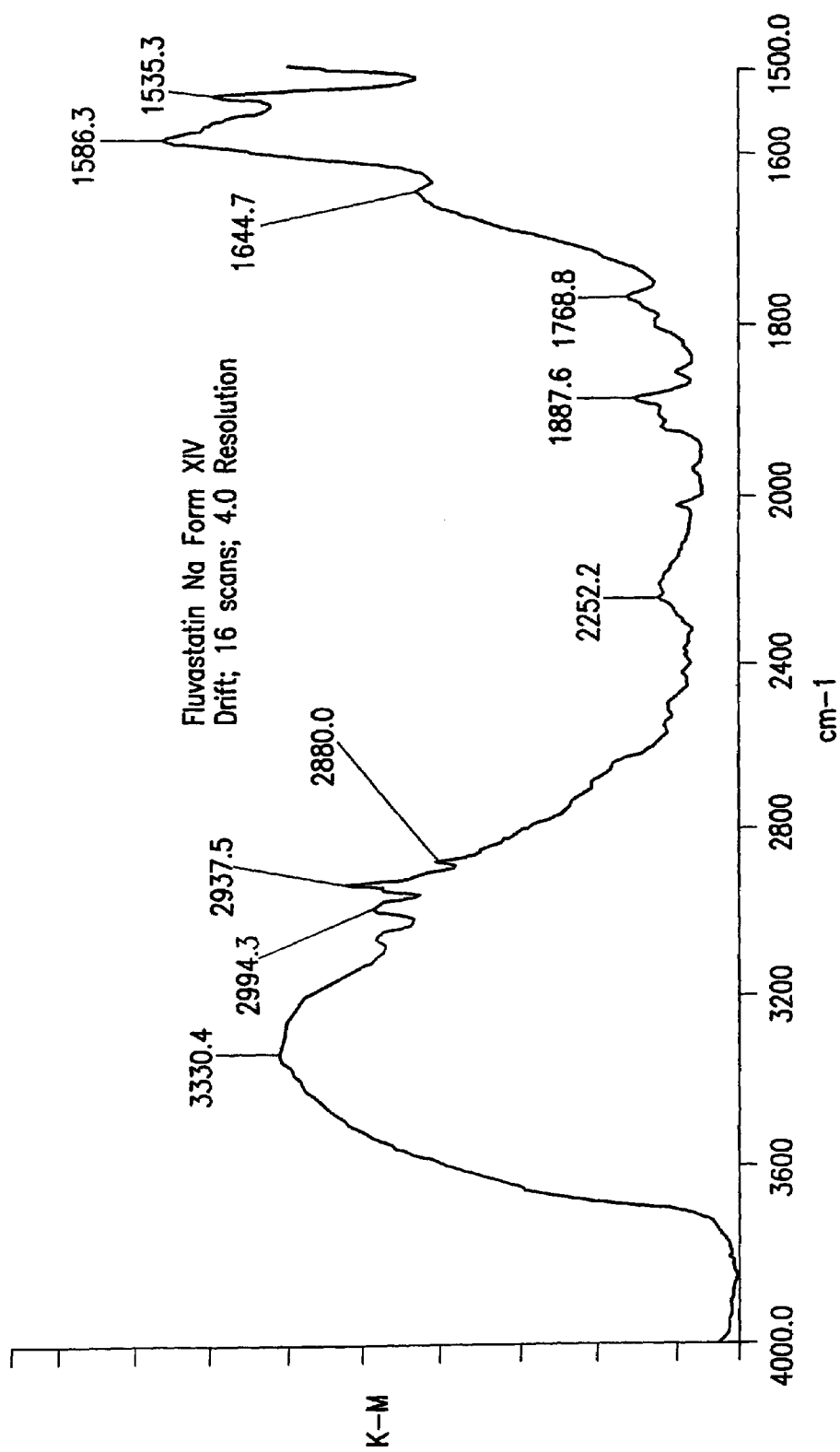
Figure 3B:
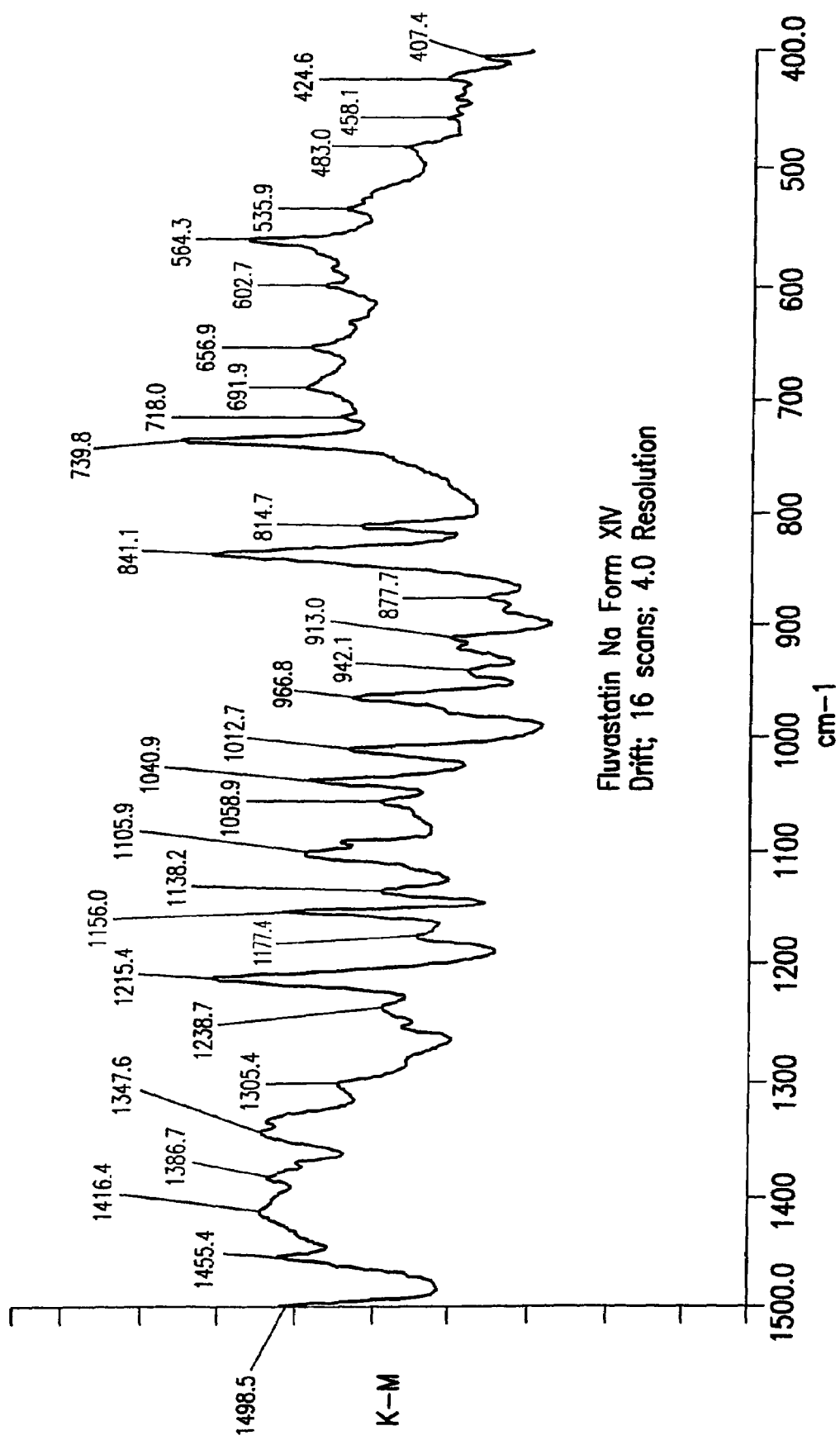
Figure 4:
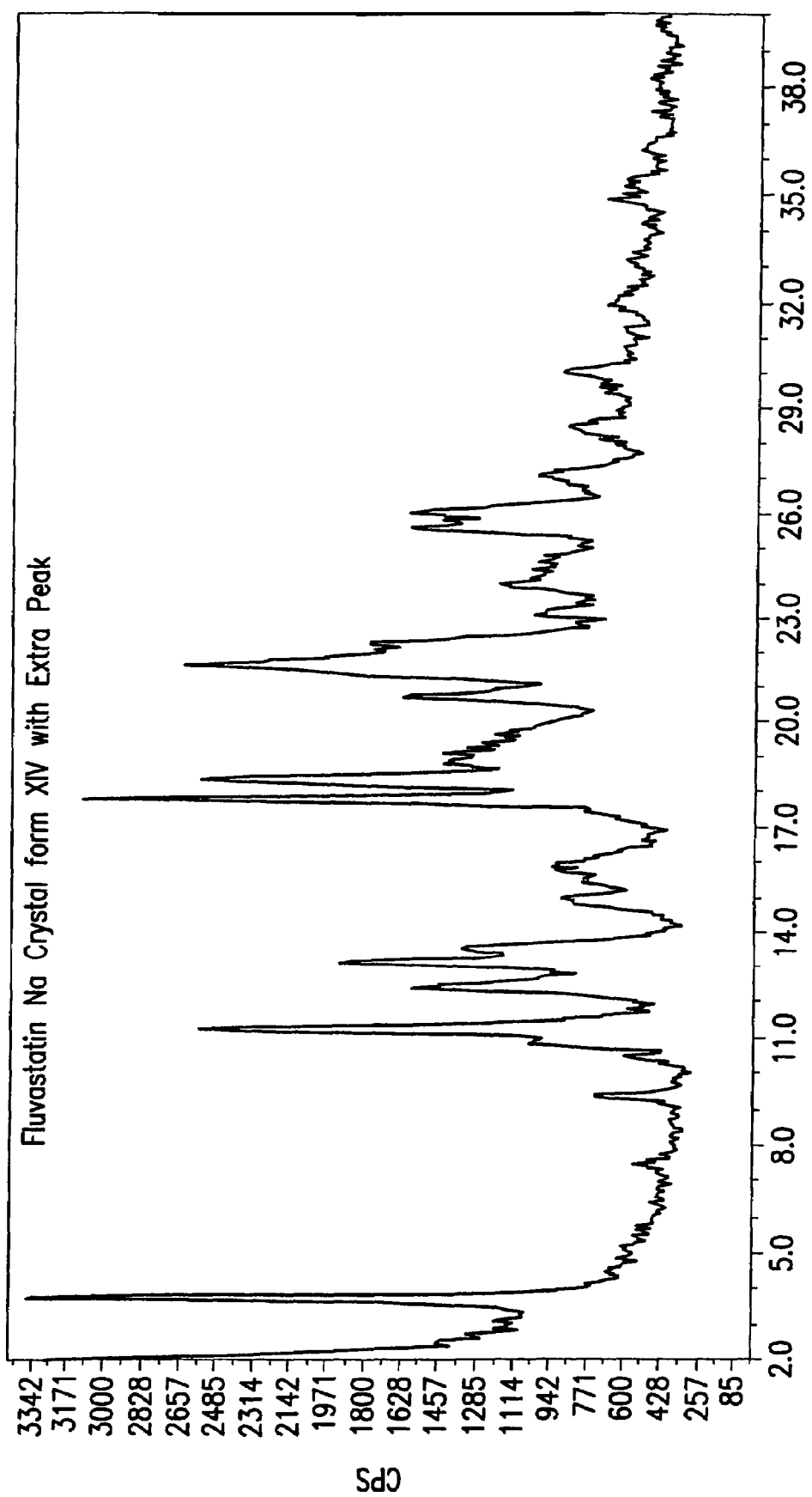
FIG. 4 depicts a powder X-ray diffractogram of fluvastatin sodium Form XIV, having an additional peak at 12.4±0.2 degrees two-theta.

Fluvastatin sodium Form XIV produces a PXRD diffractogram with characteristic peaks at 3.8, 11.1, 12.9, 17.8 and 21.7±0.2 degrees two-theta and other peaks at 9.2, 14.8, 15.7, 18.3, 20.3, 25.5 and 26.9±0.2 degrees two-theta (FIG. 1). Some crystals have all the peaks associated with Form XIV' and exhibit many of characteristics of Form XIV, but have an additional peak at 12.4±0.2 degrees two-theta (FIG. 4). Fluvastatin sodium Form XIV produced the DSC thermogram shown in FIG. 2, in which two main endothermic peaks can be seen below 90° C. and at about 110° C. The water content of the sample is about 7.1 wt. %. The loss on drying by TGA is 7.5 wt. %. Fluvastatin sodium Form XIV was stable after exposure to relative humidities between 0-100% RH for 8 days and equilibrated at water contents of about 3-17%. Fluvastatin Form XIV is in monohydrate, sesquihydrate, dihydrate, hemipentahydrate, trihydrate, tetrahydrate, and pentahydrate forms. The IR spectrum of fluvastatin sodium Form XIV is shown in FIGS. 3, 3a and 3b.

Form XIV has the appearance of a white to pale yellow powder. Stability studies have shown that its appearance does not change after storage at 40° C. for three months.

The present invention further provides a fluvastatin sodium Form XIV, of which no more than about 5% transforms into Form B upon storage at a temperature of 25, 40 and 55° C., for at least 3 months (see table 1).

TABLE 1

Stability study of Form XIV
Polymorph content by X-Ray Powder Diffraction analysis

| | | Results | | |
|---|---|---|---|---|
| Time interval | t = 0 | 25° C., 60% RH | 40° C., 75% RH | 55° C. |
| | XIV | | | |
| 1M | | XIV | XIV | XIV |
| 2M | | XIV | XIV | XIV |
| 3M | | XIV | XIV | XIV |

Fluvastatin sodium Form XIV can be prepared by suspending fluvastatin sodium in a mixture of toluene and a $C_5$ to $C_7$ straight or branched saturated hydrocarbon such as hexanes to obtain a slurry, i.e., a heterogeneous mixture, for a period of time necessary to effect the conversion and then separating Form XIV from the mixture. Form XIV also can be prepared by storing Form VII under 100% RH for 11 days.

Fluvastatin sodium Form XIV also can be prepared directly from a straight or branched lower alkyl ester of fluvastatin. The starting material is dissolved in a solution containing about 1 molar equivalent of sodium hydroxide in a solvent system selected from the group consisting of ethanol, mixtures of water and ethanol, propan-2-ol and mixtures of water and propan-2-ol, mixtures of THF and water and mixtures of propan-1-ol and water. Preferred mixtures contain about 8-9% water and 91-92% organic solvent, except for THF:water mixtures for which the mixture preferably contains about 5% water. The starting material preferably is dissolved at elevated temperature, e.g. the reflux temperature of the solvent system. At elevated temperature, an anti-solvent selected from the group consisting of acetonitrile, hexanes, dichloromethane and MTBE is added at elevated temperature to the solution to induce precipitation of Form XIV. Alternatively, the anti-solvent may be omitted and precipitation induced by cooling from some solvent systems, such as propan-2-ol:water mixtures. After allowing the resulting mixture to cool, Form XIV can be separated from the solvent system and anti-solvent by conventional techniques such as filtering, decanting, centrifuging and the like, preferably filtering under an inert atmosphere like nitrogen. The separated Form XIV may be dried. A suitable drying condition is 50° C. under vacuum.

According to an alternative process, Form XIV is prepared from a straight or branched lower alkyl ester of fluvastatin by hydrolyzing the starting material in a solution containing about 1 molar equivalent of sodium hydroxide in a solvent system containing water and an organic solvent selected from the group consisting of methanol, ethanol and THF. After hydrolysis, the organic solvent is evaporated and, optionally, more water is added, the aqueous solution may be extracted with a water immiscible solvent such as ethyl acetate and Methyl t-Butyl Ether (MTBE). Then the water is evaporated and the residue is taken up in acetonitrile and allowed to recrystallize from the acetonitrile to yield Form LXXXVII. If the amount water remaining after evaporation step is too low, then Form B is obtained. Preferably after evaporation amount of water remaining is at least about 1 mL per gram of fluvastatin sodium. Form LXXXVII can be separated from the acetonitrile by conventional techniques such as filtering, decanting, centrifuiging and the like, preferably filtering under an inert atmosphere like nitrogen. The separated Form LXXVII may than be dried to obtain Form XIV. A suitable drying condition is about 30° C. to about 60° C., such as about 40° C. or about 50° C., more preferably under vacuum. A preferred vacuum pressure is below about 100 mmHg, more preferably below about 50 mmHg.

Form XIV may also be prepared by adding portion wise MTBE, hexane, acetonitrile or dichloromethane, to a solution of fluvastatin sodium in ethanol, propan-2-ol or tetrahydrofuran as a solvent, wherein the solution is heated before, during or after of the addition, and recovering the crystalline form. An example of portion wise addition is dropwise. In one embodiment, the anti-solvents are added dropwise, followed by heating, followed by cooling and stirring to recover the crystalline form. The solvent may contain water, preferably less than about 10% by volume. In another embodiment, Form XIV is prepared by combining a solution of fluvastatin sodium in water with iso-propyl alcohol, ethyl acetate, acetonitrile or acetone. After addition, the reaction mixture may be stirred and the crystals recovered by conventional manner.

Form XIV can be prepared in high purity by the foregoing processes. In addition to being polymorphically pure, crystallization of fluvastatin sodium into Form XIV is especially effective at removing impurities. For instance, HPLC of samples of Form XIV shows that it typically contains less than 0.5% of hydroxy epimers of fluvastatin and less than 1% total impurities. HPLC was performed according to the method of *Pharmacopeial Previews*, 1999, 24, 8420.

Form XIV also can be prepared directly from a straight or branched lower alkyl ester of fluvastatin, such as a $C_1$ to $C_4$ ester. Examples of esters include methyl, ethyl, I-propyl and t-butyl. The ester is combined with water and acetonitrile, followed by the addition of sodium hydroxide. The preferred ratio of the ester and water is about 1:1.3-1:2 (Kg/L), most preferably, the ratio is about 1:1.3-1:1.8 (Kg/L). The preferred ratio of the ester and acetonitrile is preferably about 1:4-6 (Kg/L), more preferably about 1:5-6 (Kg/L). The weight is calculated based on the ester, preferably a butyl ester. After addition of sodium hydroxide, the ester is hydrolyzed and a solution eventually forms.

The sodium hydroxide used may be either aqueous or solid. When an aqueous sodium hydroxide is used, the water present in such aqueous solution is taken into account in the ratio.

Additional acetonitrile is then combined with the solution to precipitate fluvastatin sodium. The final ratio of fluvastatin to acetonitrile is preferably 1:15-1:25 (Kg/L), more preferably about 1:19.5 to 1:20.5 (Kg/L).

In the specific example provided, precipitation occurred spontaneously after addition of acetonitrile, but the solution was maintained to increase yield. The solution is preferably maintained for about 2 to about 24 hours, more preferably for about 5 hours. The process of the present invention encompasses non-spontaneous precipitation after addition of acetonitrile to the solution. Form XIV may be recovered from the reaction mixture by conventional techniques such as filtering, decanting, centrifuging and the like, preferably filtering under vacuum. The recovered Form XIV may be washed, preferably with acetonitrile and dried. A suitable drying condition is about 40° C. under vacuum.

In addition to starting with the ester, the process may be carried out from a solution of fluvastatin sodium in the mixture of water and acetonitrile.

Crystal Form XIV is useful inter alia for purification of fluvastatin. It is also useful as a pharmaceutical composition.

The particle size distribution (PSD) of the forms can be studied by several techniques. The most common PSD techniques include sieving, sedimentation, electozone sensing (Coulter Counterj, microscopy and Low angle Laser Light Scattering (LLALLS). Fluvastatin sodium Form XUV preferably has a maximal particle size of less than about 400 µm, more preferably less than about 300 µm, more preferably less than about 200 µm, more preferably less than 100 µm, more preferably less than 50 µm. The maximal size can be seen under an optical microscope.

Pharmaceutical Compositions and Dosage Forms Containing—and Methods of Medical Treatment Using The Novel Fluvastatin Sodium Forms Fluvastatin exerts an antihypercholesterolemia and antihyperlipidemia effect in mammals, especially humans. Accordingly, fluvastatin sodium Forms XIV, are useful for delivering fluvastatin to the gastrointestinal tract, bloodstream and liver of humans and other mammals suffering from or at risk of atherosclerosis. In particular, they are useful as active ingredients in pharmaceutical compositions and dosage forms. For this purpose, they may be formulated into a variety of compositions and dosage forms for administration to humans and animals.

Pharmaceutical compositions of the present invention contain fluvastatin sodium Form XIV or mixtures thereof with other crystalline forms of fluvastatin sodium, optionally in mixtures with one or more other active ingredient(s). In addition to the active ingredient(s), the pharmaceutical compositions of the present invention may contain one or more excipients. Excipients are added to the composition for a variety of purposes.

Diluents increase the bulk of a solid pharmaceutical composition and may make a pharmaceutical dosage form containing the composition easier for the patient and care giver to handle. Diluents for solid compositions include, for example, microcrystalline cellulose (e.g. Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form like a tablet may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flow properties of non-compacted solid composition and improve the accuracy of dosing. Excipients that may function as glidants include colloidal silicon dioxide, magnesium trisilicate, powdered cellulose, starch, talc and tribasic calcium phosphate.

When a dosage form such as a tablet is made by compaction of a powdered composition, the composition is subjected to pressure from a punch and die. Some excipients and active ingredients have a tendency to adhere to the surfaces of the punch and die, which can cause the product to have pitting and other surface irregularities. A lubricant can be added to the composition to reduce adhesion and ease release of the product from the die. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, fluvastatin sodium Form XIV and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chonidrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

A liquid composition according to the present invention may also contain a buffer such as guconic acid, lactic acid, citric acid or acetic acid, sodium guconate, sodium lactate, sodium citrate or sodium acetate.

Selection of excipients and the amounts to use may be readily determined by the formulation scientist based upon experience and consideration of standard procedures and reference works in the field.

The solid compositions of the present invention include powders, granulates, aggregates and compacted compositions. The dosage forms include dosage forms suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and lozenges as well as liquid syrups, suspensions and elixirs.

An especially preferred dosage form of the present invention is a capsule containing the composition, preferably a powdered or granulated solid composition of the invention, within either a hard or soft shell. The shell may be made from gelatin and optionally contain a plasticizer such as glycerin and sorbitol, and an opacifying agent or colorant. An especially preferred capsule filling contains, in addition to one or more of the fluvastatin sodium crystalline forms of this invention, the excipients magnesium stearate; microcrystalline cellulose, pregelatinized starch, sodium lauryl sulfate and talc.

Another especially preferred dosage form of this invention is a compressed tablet that contains, in addition to one or more of the fluvastatin sodium crystalline forms of this invention, the excipients microcrystalline cellulose, hydroxypropyl cellulose, hydroxypropylmethyl cellulose, potassium bicarbonate, povidone, magnesium stearate, iron oxide yellow, titanium dioxide and polyethylene glycol 8000.

The active ingredient and excipients may be formulated into compositions and dosage forms according to methods known in the art.

A composition for tableting or capsule filing may be prepared by wet granulation. In wet granulation some or all of the active ingredients and excipients in powder form are blended and then further mixed in the presence of a liquid, typically water, that causes the powders to clump up into granules. The granulate is screened and/or milled, dried and then screened and/or milled to the desired particle size. The granulate may then be tableted or other excipients may be added prior to tableting such as a glidant and or lubricant.

A tableting composition may be prepared conventionally by dry blending. For instance, the blended composition of the actives and excipients may be compacted into a slug or a sheet and then comminuted into compacted granules. The compacted granules may be compressed subsequently into a tablet.

As an alternative to dry granulation, a blended composition may be compressed directly into a compacted dosage form using direct compression techniques. Direct compression produces a more uniform tablet without granules. Excipients that are particularly well suited to direct compression tableting include microcrystalline cellulose, spray dried lactose, dicalcium phosphate dihydrate and colloidal silica. The proper use of these and other excipients in direct compression tableting is known to those in the art with experience and skill in the particular formulation challenges of direct compression tableting.

A capsule filling of the present invention may comprise any of the aforementioned blends and granulates that were described with reference to tableting, only they are not subjected to a final tableting step.

Capsules, tablets and lozenges and other unit dosage forms preferably contain a dosage equivalent to from about 10 to about 100 mg fluvastatin. Preferably the dosage is equivalent to from about 20 to about 80 mg of fluvastatin. More particularly, immnmediate or uncontrolled release dosage forms preferably contain the equivalent of from abut 20 to about 40 mg of fluvastatin and extended release dosage forms preferably contain the equivalent of from about 60 to about 100 mg of fluvastatin, more preferably about 80 mg of fluvastatin.

Having thus described the present invention with reference to certain preferred embodiments, the processes for producing Fluvastatin sodium Forms XIV of the present invention and techniques suitable for identifying them are further illustrated by the examples which follow. These examples are provided for illustrative purposes only and are not intended to limit the invention in any way.

EXAMPLES

General

Powder X-ray diffraction data were obtained using methods known in the art on a SCINTAG powder X-ray diffractometer model XTRA equipped with a solid state detector. Copper radiation of 1.5418 Å was used. A round aluminum sample holder with zero background was used. Detection limit: about 5% Form B.

DSC analysis was done on a Mettler 821 Star e. The weight of the samples was about 5 mg; the samples were scanned at a rate of 10° C./min from 30° C. to 200° C. The oven was constantly purged with nitrogen gas at a flow rate of 40 ml/min. Standard 40 μl aluminum crucibles covered by lids with 3 holes were used.

TGA analysis was done using a Mettler M3 meter. The weight of the samples was about 10 mg; the samples were scanned at a rate of 10° C./min from 25° C. to 200° C. The oven was constantly purged with nitrogen gas at a flow rate of 40 ml/min. Standard 70 μl alumina crucibles covered by lids with 1 hole were used.

IR analysis was done using a Perkin Elmer "Spectrum One" FT-IR spectrometer in DRIFTt mode. The samples in the 4000-400 cm-1 interval were scanned 16 times with 4.0 cm-1 resolution.

The water content of fluvastatin sodium is measured by the methods known in the art like Karl Fisher or thermogravimetric analysis.

Those skilled in the art will recognize the abbreviations used in the disclosure, as they are in widespread use in the fields of medicinal and organic chemistry. The abbreviations used include the following:

| ACN | acetonitrile |
| --- | --- |
| DMF | N,N-dimethyl formamide |
| DMSO | dimethyl sulfoxide |
| EtOH | ethanol |
| Et$_2$O | diethyl ether |
| EtOAc | ethyl acetate |
| IPA | isopropyl alcohol |
| MeOH | methanol |
| MTBE | methyl tert-butyl ether |
| MEK | methyl ethyl ketone |
| THF | tetrahydrofuran |

Preparative

All the preparations described below were carried out on fluvastatin sodium Form B except where indicated otherwise.

Preparation of Fluvastatin Sodium Crystal Form XIV

Example 1

Fluvastatin sodium (3.0 g) was suspended in a mixture of toluene (60 ml) and hexanes (60 ml) at reflux temperature for 19 h. Then, the mixture was cooled to room temperature. The product was isolated by filtration under nitrogen, washed with hexanes (2×10 ml) and dried at 50° C. in a vacuum oven for 22 h to obtain 1.2 g (39%) of fluvastatin sodium crystal Form XIV.

Example 2

Fluvastatin methyl ester (3.0 g) was added to a solution of NaOH (1 eq.) in water (0.75 ml) and ethanol (7.5 ml). The mixture was heated to reflux and stirred until the starting material was no longer detectable by HPLC. Then, 58 ml of MTBE was dripped into the solution over 1.5 h. Turbidity appeared in the solution. The mixture was cooled slowly to room temperature and stirred overnight. The product was isolated by filtration under nitrogen, washed with MTBE (50 ml) and dried at 50° C. in a vacuum oven for 24 h to obtain 2.21 g (72.3%) of fluvastatin sodium Form XIV.

Example 3

Fluvastatin methyl ester (2.0 g) was added to a solution of NaOH (1 eq.) in ethanol (15 ml). The mixture was stirred at about 70° C. for 1.75 h, after which the starting material was no longer detectable by HPLC. Then, 40 ml of MTBE was dripped into the solution. The mixture was cooled slowly to room temperature and stirred overnight. The product could not be filtrated so another 100 ml of MTBE was added and the mixture was stirred over the weekend. The product was isolated by filtration under nitrogen and dried at 50° C. in a vacuum oven for 24 h to obtain 1.45 g (71.2%) of fluvastatin sodium Form XIV.

Example 4

Fluvastatin methyl ester (2.0 g) was added to a solution of NaOH (1 eq.) in propan-2-ol (15 ml). The mixture was stirred at about 70° C. for 2 h, after which time the starting material was no longer detectable by HPLC. Then, acetonitrile (40 ml) was dripped into the mixture. The mixture was cooled slowly to room temperature and stirred overnight. The product was isolated by filtration under nitrogen, washed with acetonitrile (50 ml) and dried at 50°C in a vacuum oven for 24 h to obtain 1.54 g (75.5%) of fluvastatin sodium Form XIV.

Example 5

Fluvastatin methyl ester (3.0 g) was added to a solution of NaOH (1 eq.) in water (0.75 ml) and propan-2-ol (7.5 ml). The mixture was heated to reflux and 1 ml of propan-2-ol was added. After 2 h, the mixture was cooled to room temperature and stirred for 2 h. MTBE (60 ml) was dripped into the solution over 20 min and the resulting mixture was stirred for another 1.5 h. The product was isolated by filtration under nitrogen, washed with MTBE and dried at 50° C. in a vacuum oven for 24 h to obtain 1.9 g (62%) of fluvastatin sodium Form XIV.

Example 6

Fluvastatin sodium (3.0 g) was dissolved in a mixture of propan-2-ol (50 ml) and water (5 ml) at reflux temperature. MTBE (50 ml) was added dropwise and the mixture was stirred at reflux temperature for ½ h. Then, the mixture was cooled to room temperature and stirred at this temperature for 16 h. Another portion of MTBE (50 ml) was added to obtain further precipitation. After 5 h, the product was isolated by filtration under nitrogen, washed with MTBE (2×10 ml) and dried at 50° C. in a vacuum oven for 24 h to obtain fluvastatin sodium Form XIV (1.4 g, 48%).

Example 7

Fluvastatin sodium (30.0 g) was dissolved in a mixture of propan-2-ol (500 ml) and water (50 ml) at reflux temperature. The obtained solution was stirred at reflux temperature for 1.5 h. Then, the mixture was cooled to room temperature and stirred at this temperature for 16 h. The product was isolated by filtration under nitrogen, washed with propan-2-ol (2×100 ml) and dried at 50° C. in a vacuum oven for 23 h to obtain fluvastatin sodium Form XIV (14.8 g, 49%).

Example 8

Fluvastatin sodium (3.0 g) was dissolved in a mixture of propan-1-ol (30 ml) and water (3 ml) at reflux temperature. MTBE (60 ml) was added dropwise and the mixture was stirred at reflux temperature for 1 h. Then, the mixture was cooled to room temperature and stirred at this temperature for 3 h. The product was isolated by filtration under nitrogen, washed with MTBE(2×15 ml) and dried at 50° C. in a vacuum oven for 20 h to obtain fluvastatin sodium Form XIV (2.2 g, 74%).

Example 9

Fluvastatin sodium (4.0 g) was dissolved in a mixture of THF (20 ml) and water (1 ml) at reflux temperature. MTBE (40 ml) was added dropwise and the mixture was stirred at reflux temperature for 1 h. Then, the mixture was cooled to room temperature and stirred at this temperature for 4.5 h. The product was isolated by filtration under nitrogen, washed with MTBE (2×20 ml) and dried at 50° C. in a vacuum oven for 24 h to obtain fluvastatin sodium Form XIV (1.9 g, 47%).

Example 10

Fluvastatin sodium (4.0 g) was dissolved in a mixture of THF (20 ml) and water (1 ml) at reflux temperature. Dichloromethane (40 ml) was added dropwise and the mixture was stirred at reflux temperature for 40 minutes. Then, the mixture was cooled to room temperature and stirred at this temperature for 24 h. The product was isolated by filtration under nitrogen, washed with dichloromethane (2×20 ml) and dried at 50° C. in a vacuum oven for 24 h to obtain fluvastatin sodium Form XIV (3.8 g, 94%).

Example 11

Fluvastatin sodium (4.0 g) was dissolved in a mixture of THF (20 ml) and water (1 ml) at reflux temperature. Hexanes (40 ml) was added dropwise and the mixture was stirred at reflux temperature for 40 minutes. Then, the mixture was cooled to room temperature and stirred at this temperature for 4 h. The product was isolated by filtration under nitrogen, washed with Dichloromethane (2×20 ml) and dried at 50° C. in a vacuum oven for 24 h to obtain fluvastatin sodium Form XIV (2.6 g, 66%).

Example 12

A 250 ml round bottom flask was loaded with fluvastatin (20.0 g, 47 mmole), water (60 ml) and ethanol (100 ml) and NaOH (1.94 g). The mixture became clear and was stirred until the raw material wasn't observed by HPLC. The solution was filtered and the EtOH was distilled. Water (157 ml) was added to the slurry mixture, which was extracted with EtOAc (2×100 ml). The clear solution was divided to 6 parts.

Example 13

A solution of fluvastatin sodium that was prepared as described in Example 12 (42 ml) was concentrated until the water volume was ca. 1.5 ml then IPA (68 ml) was added and the mixture was stirred at room temperature for 18 h. The product was isolated by filtration under nitrogen, washed with IPA (20 ml) and dried at 40°C in a vacuum oven for 24 h to obtain 1.12 g (ca. 33%) of fluvastatin sodium crystal Form XIV.

Example 14

A solution of fluvastatin sodium that was prepared as described in Example 12 (42 ml) was concentrated until the water volume was ca. 1.8 ml then acetonitrile (68 ml) was added and the mixture was stirred at room temperature for 17.5 h. The product was isolated by filtration under nitrogen, washed with acetonitrile (20 ml) and dried at 40°C in a vacuum oven for 24 h to obtain 2.18 g (ca. 64%) of fluvastatin sodium crystal Form XIV (Form B: non-detectable).

Example 15

A solution of fluvastatin sodium that was prepared as described in Example 12 (42 ml) was concentrated until the water volume was ca. 0.8 ml then acetone (68 ml) was added and the mixture was stirred at room temperature for 24.5 h. The product was isolated by filtration under nitrogen, washed with acetone (20ml) and dried at 40° C. in a vacuum oven for 22 h to obtain 2.65 g (ca. 78%) of fluvastatin sodium crystal Form XIV.

Example 16

Acetonitrile (30 ml) and brine (15 ml) added to solution of Fluvastatin sodium that was prepared as described in example 12 (30 ml) The phases were separated and the organic phase was extracted with brine (15 ml), then acetonitrile (30 ml) was added to the organic phase which was stirred at room temperature over night. The product was isolated by filtration under nitrogen, washed with acetonitrile (30 ml) and dried at 40° C. in a vacuum oven for 24 h to obtain 1.99 g (ca. 80%) of fluvastatin sodium crystal Form XIV (+NaCl residue).

Example 17

EtOAc (32 ml) and brine (16 ml) added to solution of fluvastatin sodium that was prepared as described in Example 12 (32 ml contains ca. 3 g fluvastatin sodium) The phases were separated and the organic phase was extracted with brine (10 ml), then EtOAc (32 ml) was added to the organic phase which was stirred at room temperature over night. The product was isolated by filtration under nitrogen, washed with EtOAc (90 ml) and dried at 40° C. in a vacuum oven for 24 h to obtain 2.43 g (ca. 80%) of fluvastatin sodium crystal Form XIV (+NaCl residue).

Example 18

A 250 ml round bottom flask was loaded with fluvastatin tert-butyl ester (3.0 g, 6.4 mmole), water (27 ml), THF (7.5 ml) and NaOH (0.29 g). The mixture was stirred for 1.5 h then THF (2.5 ml) was added. After another 0.5 h THF (2.5 ml) was added again and the solution became clear. The solution was stirred for another 5 h then extracted with EtOAc (2×20 ml). The clear solution was divided to 2 parts.

Example 19

A solution of fluvastatin sodium that was prepared as described in Example 18 was concentrated until the weight was 1.51 g then acetonitrile (30 ml) was added and the mixture was stirred at room temperature over night. The product was isolated by filtration under nitrogen flow, washed with acetonitrile and dried at 40° C. in a vacuum oven for 24 h to obtain 0.56 g (ca. 40%) of fluvastatin sodium crystal Form XIV.

Example 20

A solution of fluvastatin sodium that was prepared as described in Example 18 was concentrated until the weight was 1.5 g, then acetone (30 ml) was added and the mixture was stirred at room temperature over night. The product was isolated by filtration under nitrogen flow, washed with acetone and dried at 40° C. in a vacuum oven for 24 h to obtain 1 g (ca. 72%) of fluvastatin sodium crystal Form XIV.

Example 21

Water (56 ml), acetonitrile (200 ml) and FDE-tBu (40 gr) were added to a 1 L stirred reactor. At 25° C., 7.5 gr of 47% NaOH solution was added, and the mixture was heated to 35° C. The mixture became clear during the hydrolysis. End of reaction was determined by HPLC (~3-4 hr). The mixture was then cooled to 25° C. Acetonitrile (600 ml) was added to the mixture. The mixture was stirred for ~5 hr to increase yield, and the formed precipitate was filtered under vacuum. The wet product was washed with 120 ml of acetonitrile. The wet product was dried in a vacuum oven at 40° C. to obtain FLV Na form XIV crystals (Yield: 87%).

Preparation of Fluvastatin Sodium Crystal Form XIV, Having a Peak at 12.4±0.2 Degrees two-theta in the XRD Pattern Example 22

A 100 ml round bottom flask was loaded with fluvastatin tert-butyl ester (4.0 g, 8.56 mmole), MeOH (24 ml) and NaOH (0.35 g) in water (2 ml). The mixture was heated to 35° C. After 2 h water (10 ml) was added and the mixture was stirred for another 4.5 h then the MeOH was evaporated.

The volume of the water was completed to 8 vol. and the mixture was extracted with EtOAc (24 ml). The aqua solution was evaporated to contain ca. 1 vol. water and ACN (60 ml) was added. The solution was stirred at room temperature over night. The product was isolated by filtration under nitrogen, washed with ACN (15 ml) and dried at 40° C. in a vacuum oven for 24 h to obtain 3.18 g (85.7%) of fluvastatin sodium crystal form XIV, having a peak at 12.4±0.2 degrees two-theta in the XRD pattern Example 23

A 100 ml round bottom flask was loaded with fluvastatin tert-butyl ester (4.0 g, 8.56 mmole), MeOH (24 ml) and NaOH (0.31 g) in water (2 ml). The mixture was heated to 35° C. and stirred for 4.5 h then water (10 ml) was added and the MeOH was evaporated. The volume of the water was completed to 8 vol. and the mixture was extracted with EtOAc (25 ml). The aqueous solution was evaporated to contain ca. 1 vol. water and ACN (60 ml) was added. The solution was stirred at room temperature over night. The product was isolated by filtration under nitrogen, washed with ACN and dried at 40° C. in a vacuum oven for 24 h to obtain 1.06 g (28.6%) of fluvastatin sodium crystal form XIV, having a peak at 12.4±0.2 degrees two-theta in the XRD pattern.

Preparation of Fluvastatin Sodium Crystal Form XIV Through Form LXXXVII

Example 24

Into a 1 L reactor equipped with mechanical stirrer and thermometer, 40 g of fluvastatin diol tert-butyl ester and 240 ml MeOH were charged. 3.54 g of NaOH dissolved in 20 ml water were added and the mixture was heated to 35° C. After 1 hour the solution became clear and 100 ml Water were added. The reaction solution was maintained at 35° C. under mixing during 4 hours. The MeOH was distilled by vacuum at 40° C. and water (230 ml) was added in order to complete the volume to 8 volumes vs. 1 gr of fluvastatin diol tert-butyl ester. he aqueous mixture was extracted with 240 ml MTBE. After vacuum filtration the water was distilled by vacuum at 60° C. ACN (120 ml) was added at room temperature is with vigorously stirring in order to get maximum dissolving. The amount of water in the clear solution was determined by Karl Fisher method and calculated to be 1.6 vol then 680 ml of ACN were added. The reaction solution was maintained at 25° C. under mixing over night. The product was isolated by vacuum filtration under $N_2$ flow, washed with ACN (100 ml) (crystal Form LXXXVII), dried in vacuum oven at 40° C. for 25 hours to obtain 29.2 g (78.8%) fluvastatin sodium crystal Form XIV.

Example 25

Fluvastatin diol tert-butyl ester (80 g), methanol (480 ml), 47% NaOH solution (14.87 g) and water (32.1 ml) were added into a stirred reactor and heated to 35° C. When the solution became clear (~1 hr), additional water (80 ml) was added. The solution was stirred at 35° C. for additional 2 hours. Methanol was distillated by vacuum distillation at 60 mmHg and a jacket temp of 40° C. When distillation ended, ACN (240 ml) and water (54 ml) were added until dissolution occurred. ACN (680 ml) was added to half of the solution (193 g) at 25° C. The product precipitated during the ACN addition. The mixture was stirred at 25° C. for additional 12 hours, then filtered with vacuum and the wet product was washed with ACN (120 ml). XRD detection for the wet product is Form LXXXVII (Form B: non-detectable). The wet product was dried in a vacuum oven at 40° C. for 12-15 hours. XRD detection for the dry product was Form XIV.

Example 26

Fluvastatin diol tert-butyl ester (40 gr), methanol (240 ml), 47% NaOH solution (7.44 gr) and water (16.1 ml) were added into a stirred reactor and heated to 35° C. When the solution became clear (~1 hr) additional water (40 ml) was added. The solution was stirred at 35° C. for additional 2 hours. Methanol was distillated by vacuum distillation at 60 mmHg and a jacket temp of 40° C. When distillation ended, ACN (120 ml) and water (30 ml) were added until dissolution occurred. ACN (680 ml) was again added to the solution at 25° C. The product precipitated during the ACN addition. The mixture was stirred at 25° C. for additional 12 hours, then filtered with vacuum and the wet product was washed with ACN (120 ml). XRD detection for the wet product was Form LXXXVII. The wet product was dried in a vacuum oven at 40° C. for 12-15 hours. XRD detection for the dry product was Form XIV.

Example 27

500 g of Fluvastatin diol tert-butyl ester and 3000 ml of methanol were added to a 10 liter reactor and stirred at room temperature. A solution of 45.5 g of 100% NaOH and 250 ml water was added. The mixture was heated to 35-36 deg. by setting the jacket temperature to 40° C. When the mixture became a clear solution (~60 min). According to KF result, the solution contained 2.7 vol. of water (per g Fluvastatin diol tert-butyl ester)." 1250 ml of water were added. End of reaction was determined by HPLC after 90 min. Methanol was distilled at 40° C. in jacket and <60 mmHg vacuum. 2680 ml water were added and the mixture was cooled to 5° C. and stirred overnight. In the morning, 3000 ml of MTBE were added. The mixture was heated to 25° C. and stirred for 20 min. Stirring was stopped for phase separation. The aqueous phase was distilled for water removal at 60° C. and <60 mmHg vacuum. 1500 ml of ACN were added at 25° C. and the mixture became a clear solution. 1500 ml of ACN were added to the solution and the mixture was stirred at 25° C. overnight (~16 h). Precipitation occurred during ACN addition. The product was filtered with suction and washed with 1500 ml of ACN. 610 g of wet product were obtained (detected to be form 87 by XRD). Wet product was dried in a vacuum oven at 40° C. for 24 h. 380 g of dry product was obtained (detected to be form XIV by XRD).

Stability Tests

Example 28

Fluvastatin Na Form XIV was stable after exposure to relative humidities between 0-100% RH for 7 days and equilibrated at water contents between 3-16%. The results are summarized in the next table. Fluvastatin Form XIV is in monohydrate, sesquihydrate, dihydrate, hemipentahydrate, tryhydrate, tetrahydrate and pentahydrate forms.

Water uptake (%) and Crystal form of Fluvastatin Na Crystal form XIV Equilibrated at different Relative humidities for 7 days

| RH | Water content by KF (%) | Weight loss by TGA (%) | Form |
|---|---|---|---|
| 100 | 15.5 | | XIV |
| 80 | 13.2 | | XIV |
| 60 | 10.2 | | XIV |
| 40 | 7.0 | | XIV |
| 20 | 4.8 | | XIV |
| 0 | 3.2 | | XIV |
| T = 0 | 5.9 | 6.0 | XIV |

Having thus described the invention with reference to particular preferred embodiments and illustrated it with examples, those in the art may appreciate modifications to the invention as described and illustrated that do not depart from the spirit and scope of the invention as defined by the claims which follow.

What is claimed is:

1. A process for preparing a crystalline form of fluvastatin sodium characterized by a PXRD pattern with peaks at 3.8, 11.1, 12.9, 17.8 and 21.7±0.2 degrees two-theta comprising:
   a) combining a $C_1$ to $C_4$ alkyl ester of fluvastatin with acetonitrile at a ratio of about 1:4-6 (Kg/L) of the ester to acetonitrile, and with water at a ratio of about 1:1.3-1:2 (Kg/L) of the ester to the water, to obtain a mixture;
   b) combining sodium hydroxide with the mixture to hydrolyze the ester, thereby obtaining a solution, wherein if aqueous sodium hydroxide is used, the water ratio does not exceed that provided in step (a);
   c) combining additional acetonitrile with the solution to precipitate crystalline fluvastatin sodium; and
   d) recovering crystalline fluvastatin sodium.

2. The process of claim 1, wherein the alkyl ester is combined with acetonitrile at a ratio of about 1:5-6(Kg/L).

3. The process of claim 1, wherein addition of the acetonitrile in step (c) results in a ratio of about 1:15 to about 1:25 (Kg/L).

4. The process of claim 3, wherein the ratio is about 1:19.5-1:20.5 (Kg/L).

5. The process of claim 1, wherein the ratio of the ester to water is about 1:1.3-1:1.8 (Kg/L).

6. The process of claim 1, wherein the solution is maintained after addition of acetonitrile for about 2 to about 24 hours.

7. The process of claim 6, wherein the solution is maintained for about 5 hours.

8. The process of claim 1, wherein prior to combining with acetonitrile, the mixture is heated to a temperature of about 30° C. to about 40° C. to facilitate dissolution.

9. The process of claim 8, wherein the mixture is heated to a temperature of about 35° C.

10. The process of claim 8, wherein after heating, the solution is cooled to room temperature.

11. The process of claim 1, wherein the ester is t-butyl.

12. The process of claim 1, wherein if an ester other than the butyl ester is used, the ratio is based on molar weight of butyl ester, and is adjusted, by calculating molar weight of the other ester in relation to the butyl ester of fluvastatin.

13. A process for preparing a crystalline form of fluvastatin sodium characterized by a PXRD pattern with peaks at 3.8, 11.1, 12.9, 17.8 and 21.7±0.2 degrees two-theta comprising:
   a) preparing a solution of fluvastatin sodium in acetonitrile at a ratio of about 1:4-6 (Kg/L) of fluvastatin to acetonitrile, and in water at a ratio of about 1:1.3-1:2 (Kg/L) of fluvastatin to water, wherein the ratio is based on the molar weight of butyl ester of fluvastatin, and is adjusted if an ester other than the butyl ester is used, by calculating molar weight of the other ester in relation to the butyl ester of fluvastatin;
   b) combining the solution with an additional amount of acetonitrile to precipitate the crystalline fluvastatin sodium; and
   c) recovering the crystalline fluvastatin sodium.

14. The process of claim 13, wherein the fluvastatin to acetonitrile ratio is about 1:5-6 (Kg/L).

15. The process of claim 13, wherein addition of acetonitrile in step (b) results in a ratio of about 1:15-1:25 (Kg/L).

16. The process of claim 15, wherein the ratio is about 1:19.5 to 1:20.5 (Kg/L).

17. The process of claim 13, wherein the ratio of fluvastatin to water is about 1:1.3-1:1.8 (Kg/L).

* * * * *